Figure 1:
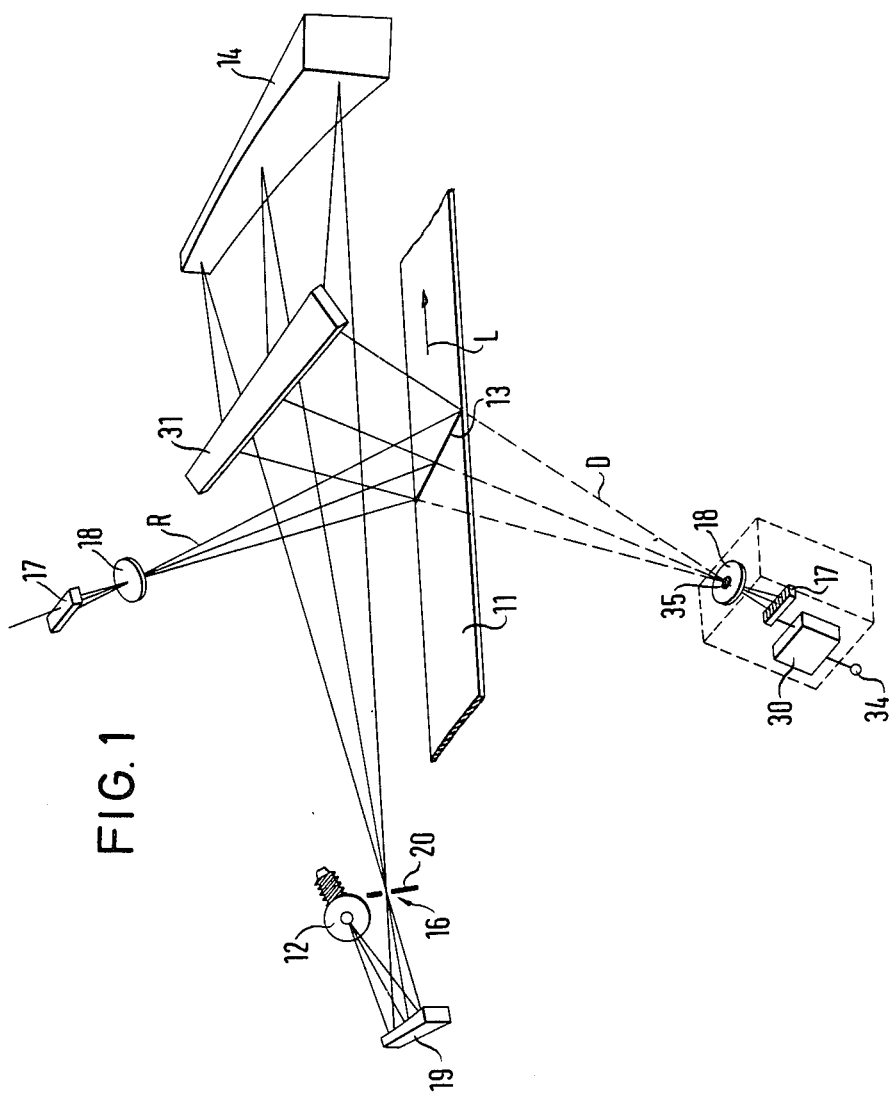

United States Patent [19]

Weber

[11] Patent Number: 4,775,238

[45] Date of Patent: Oct. 4, 1988

[54] OPTICAL WEB MONITORING APPARATUS

[75] Inventor: Klaus Weber, Königsbronn, Fed. Rep. of Germany

[73] Assignee: Erwin Sick GmbH Optik-Elektronik, Waldkirch, Fed. Rep. of Germany

[21] Appl. No.: 900,755

[22] Filed: Aug. 27, 1986

[30] Foreign Application Priority Data

Sep. 24, 1985 [DE] Fed. Rep. of Germany ....... 3534019

[51] Int. Cl.⁴ ........................................... G01N 21/88
[52] U.S. Cl. ..................................... 356/431; 250/563
[58] Field of Search ............... 356/429, 430, 431, 237; 250/562, 563

[56] References Cited

U.S. PATENT DOCUMENTS 2,798,966  7/1957  Summerhayes, Jr. .............. 250/563
3,693,021  9/1972  Lake, Jr. et al. ..................... 356/430
4,549,206  10/1985  Suzuki et al. ....................... 250/563

FOREIGN PATENT DOCUMENTS 3411934  10/1984  Fed. Rep. of Germany ...... 356/237

Primary Examiner—F. L. Evans

[57] ABSTRACT

An optical web monitoring apparatus has an illuminating arrangement which images the pupil of the source of illumination into the observing pupil of the camera objective (18) of a diode row camera using a strip-like concave mirror (14), or two strip-like concave mirrors (14, 15), and thus achieves the maximum attainable light yield. The construction is realized such that a fault seeking apparatus with a laser scanner can be used at the same time using the same mirror strips (14, 15). Thus two monitoring operations can be carried out simultaneously.

22 Claims, 2 Drawing Sheets

OPTICAL WEB MONITORING APPARATUS

The invention relates to an optical web monitoring apparatus comprising an illumination arrangement which generates, by means of a light source and a strip-like concave mirror, a strip of illumination on the surface of the web and a light receiving arrangement which projects light emerging from the illuminated strip to a photoreceiver arrangement.

Such optical web monitoring apparatus normally operates with a laser and a mirror wheel arranged at the focal point of the concave mirror, with the mirror wheel generating, via the concave mirror, a scanning light bead on the surface of the material web, which periodically scans the web transverse to its longitudinal direction or direction of movement and thus generates the strip of illumination. The light yield of such apparatuses is high because only a single sharply bundled laser light beam is used, the light of which largely reaches the photoreceiver arrangement.

The disadvantage of such a monitoring apparatus is the requirement for a mirror wheel or the like which rotates or oscillates at high speed (see for example German Offenlegungsschrift No. DE-OS 25 32 602; German Patent DE-PS No. 960 785), and the requirement for a light source with an extremely high beam density because each point in the object is only illuminated for a very short time.

The object of the invention is thus to provide an optical monitoring apparatus of the initially named kind by means of which material webs can be scanned without optical components which are mechanically and rapidly moved and which can be illuminated with classical light sources, without the advantage of a high light strength at the photoreceiver arrangement being lost.

In order to satisfy this object there is provided, in accordance with the invention, optical web monitoring apparatus comprising an illumination arrangement which generates, by means of a light source via a transmitter-side strip-like concave mirror, a strip of illumination on the surface of the web, which is preferably moved in its longitudinal direction and has a distinct spacing from the transmitter-side concave mirror, wherein the strip of illumination extends transverse to the longitudinal direction of the web preferably across the whole width thereof; and a light receiving arrangement which projects light emerging from the strip of illumination on the material web via an optical system onto a photo-receiver arrangement which delivers electrical signals corresponding to the received light to an electronic processing circuit, characterised in that the transmitter-side concave mirror which is illuminated in stationary manner by the light source, optionally with further optical image forming means, forms an image of the entry pupil for the total beam path at a location within the beam path extending from the light source to the photoreceiver arrangement, at a substantial distance behind the strip of illumination, in an objective located there; and in that the objective, optionally with the further optical image forming means, images the strip of illumination onto a line of diodes forming the photoreceiver arrangement located behind the objective in such a way that the strip-like image of the strip of illumination extends in the longitudinal direction of the line of diodes.

Thus, in accordance with the invention, the strip of illumination on the surface of the material web is imaged in greatly reduced form onto a line of diodes, which can for example be arranged within a line camera. A normal television camera can also be considered for this purpose. The light strength necessary for an adequate response of the individual photoelements of the line of diodes is ensured by the imaging of the entry pupil at the objective in accordance with the invention. With this arrangement all N diodes of the row (N = 1000 to 4000) will be simultaneously illuminated and accumulate the brightness signal until the whole line is electronically interrogated. At the same line frequency there is thus an N-times signal when compared with the laser based point scanner.

As the individual photoelements of the diode row can be electronically interrogated one after the other, the scanning frequency can be increased, as a result of the rapid switching possibilities of electronic components, to the level permitted by the intensity of illumination of the diode row before the signal/noise ratio becomes too unfavourable.

The optical image forming quality of the beam path leading from the illumination pupil into the observation pupil determines the required overlap between the image of this illumination pupil and the contrast diaphragm for the dark field which covers this image. The beam path quality, and thus the quality of the optical components along it, thus determines the smallest angular deflections produced by faults in the object which can still be detected.

On the other hand the quality of the objective of the line camera determines the quality of the image of the illuminated strip of the web or object on the diode row, and is thus the determining factor for the spatial resolution and distortion. The aperture ratio of this objective ultimately affects the brightness of the image on the receiver surface in ccordance with a square law. One thus endeavours to use a light intensive objective, the pupil of which is filled with the aid of the optical illuminating system of the invention with the image of the illuminating pupil.

In a particularly preferred embodiment a point light source is arranged at the location of the entry pupil and generates the strip of illumination via the transmitter-side concave mirror which is vignetted transverse to its longitudinal direction. Alternatively, a point light source can be imaged via a strip-like condensing concave mirror extending optically parallel to the transmitter-side concave mirror at an aperture diaphragm arranged at the location of the entry pupil, and the light emerging through the aperture diaphragm generates the strip of illumination via the vignetted transmitter-side concave mirror.

In these embodiments one requires only a single transmitter-side concave mirror, however the strip of illumination is relatively unsharp, which however, having regard to its projection onto the diode row, does not represent a substantial disadvantage for the above named reasons. It is however in any event expedient for obtaining a particularly simple construction if no further optical image forming elements are arranged between the concave mirror and the objective. In order to obtain a strip of illumination which is rather long the strip of illumination is preferably located approximately between ⅓ to ½ of the path between the transmitter-side concave mirror and the objective.

While the embodiments discussed above with a single concave mirror will generally be satisfactory for fault seeking a telecentric illumination beam path achieved using two concave mirrors has advantages in the precise detection of positions in the object. Thus, the light receiving arrangement may also have a receiver-side strip-like concave mirror which preferably has the same focal length as the transmitter-side concave mirror. This is particularly useful when detecting the geometry of patterns of the web material.

In such an arrangement the beam path between the transmitter-side concave mirror and the receiver-side concave mirror preferably extends in parallel manner.

In place of a point-like light source, or an image of such a light source in the entry pupil, a line-like light source can be imaged via a condensor and the transmitter-side concave mirror onto the surface of the material web in order to form the strip of illumination there.

It is possible, through the monitoring apparatus of the invention, to detect faults with small beam deflection down to the size of the image of a single diode of the row in the object. Because the illumination does not take place with a laser but instead preferably with white light, colour deviations can also be detected—using several diode rows in a colour TV camera arrangement.

If however, faults which are substantially smaller should also be detected, which will in general produce larger scattering of light, the monitoring apparatus of the invention can also be combined with a laser scanner, with the two beam paths being interleaved.

For this purpose a beam divider is provided between the entry pupil and the transmitter-side concave mirror; and a scanning beam, generated by a mirror wheel, rotary mirror or the like arranged at a distance from the transmitter-side concave mirror corresponding to the focal length and by a laser, reaches the transmitter-side concave mirror from where the scanning beam is projected obliquely onto the material web in the region of the strip of illumination.

The laser scanner is particularly suitable for detecting the smallest faults with large scattering angles. The diode row however recognises more extended faults with smaller angles of scattering.

In order to prevent the light of the one beam path entering into the photoreceiving arrangement of the other the two interleaved beam paths should be decoupled by optical filters and/or dichromatic dividing mirrors which are tuned to non-overlapping spectral ranges.

The image forming conditions are preferably selected such that the scale of the image of the entry pupil in the objective amounts to 0.5:1 to 1:2 and is in particular approximately 1:1.

In order to achieve more compact arrangements folded beam paths are expediently used in suitable manner, for which purpose plane strip-like deflecting mirrors can be provided in the beam path.

It is particularly advantageous if diaphragms which are matched to one another are provided in the entry pupil and in the objective. In this way certain types of fault can be reproduced with a particularly good contrast. Diaphragms can in particular be arranged so that a dark field free of azimuth effect, an arrangement of streaks, or a dark field with an intentional azimuth effect, is realised with high sensitivity.

Figure 2:
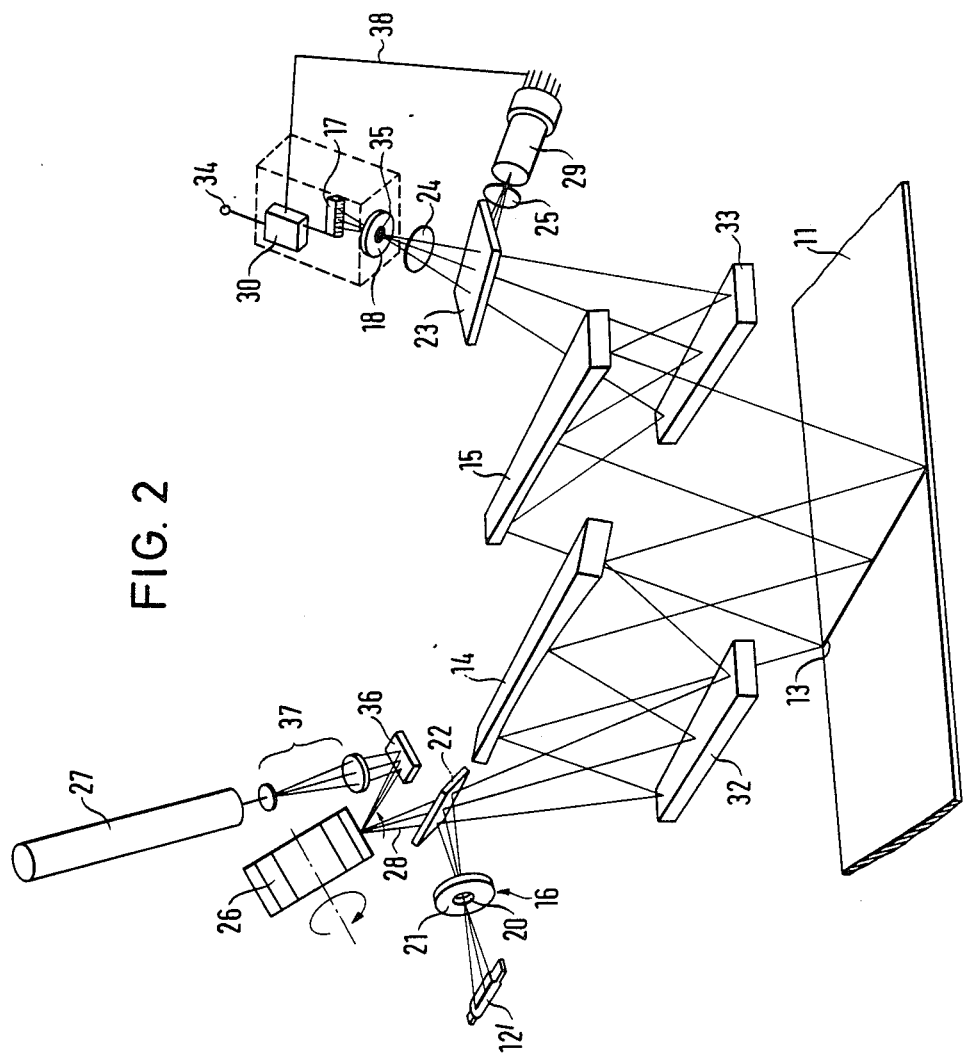

The invention will now be described in the following by way of example and with reference to the drawings which show:

FIG. 1 in schematic perspective illustration a first preferred embodiment of a monitoring apparatus in accordance with the invention, and FIG. 2 in schematic perspective representation a further embodiment, wherein a laser scanner is additionally integrated into the optical monitoring apparatus of the invention.

As seen in FIG. 1 a relatively narrow and short strip-like condensing concave mirror 19 images a point light source 12 into an aperture diaphragm 20 which determines the entry pupil 16 for the entire beam path. A strip like transmitter-side concave mirror 14 is arranged at a distance equal to its radius of curvature from the aperture diaphragm 20 optically parallel to the condensing strip-like concave mirror 19 in such a way that its spherically curved surface is fully illuminated by the light emerging from the aperture diaphragm 20. The convergent reflected light from the concave mirror 14 is deflected via a deflecting mirror 31 obliquely downwardly onto the surface of a material web 11 where the incident light generates a strip of light or illuminated strip 13 extending transverse to the longitudinal direction and direction of movement L of the web. The beam path D behind the material web 11 is only indicated in broken lines because the light beams incident in the region of the strip of illumination 11 only pass through the material web 11 at points where holes are located, unless one is concerned with a transparent film.

A reflected beam R is also drawn in which is reflected at the angle of reflection from the strip of illumination 13 and which converges at a point in an objective 18. In corresponding manner the transmitted light beam D indicated in broken lines behind the web converges at a further objective 18 for transmitted light.

Diode rows 17 are arranged behind the objectives 18 at a spacing from the objectives 18 such that a sharp image of the strip of illumination 13 is generated on the photosensitive surface of the diode rows 17.

An electronic processing circuit 30 is connected to the diode rows, is however only schematically illustrated in FIG. 1 for the lower diode row 17, and transmits error signals at an output 34. A corresponding electronic processing circuit is also connected to the upper diode row 17.

In order to make a dark field evaluation possible a circular diaphragm 35 which is not permeable to light is provided at the centre of the lower objective 35 onto which the light passing through the web 11 is concentrated. If the material web 11 is a foil then all the light passing through the foil is intercepted by the circular diaphragm 35. Only at positions where a light deflecting fault is located in the material web 11, which is constructed as a foil, does light deflection take place in such a way that these light beams can pass past the circular diaphragm 35 and enter into the objective 18, and thus reach the diode row 17. In this manner a very sensitive fault indication takes place.

A corresponding circular diaphragm 35 could also be provided in the upper objective 18 if, for example, light reflecting sheet metal webs are used as a material web 11. In this case the normally reflected light does not reach the diode row 17 but only light beams deflected by faults past the circular diaphragm 35.

The reproduction of the strip of light 13 on the surface of the material web 11 is not an exact image; on the contrary the light beam determined by the width and length of the transmitter-side concave mirror 14 generates a strip of illumination 13 which is narrower and shorter than the transmitter-side concave mirror 14 in accordance with the convergence of the light beam in the direction towards the objective 18. The size of the transmitter-side concave mirror 14 must be so selected, taking account of the strip of illumination 13, that the strip of illumination just extends over the full width of the web 11.

The objective 18 of the line camera is focussed onto the material web at the location of the strip of illumination 13. The image portion of the material web 11 which falls on each individual diode thus contributes, by its brightness, to information concerning this point of the object, and thus also to information on faults which are present there. The imaginary diode row projected by the objective 18 against the light direction onto the material web thus forms, through the images of the individual diodes, the raster for the spatial resolution for the fault notifications.

The individual photoelements of the diode rows 17 are preferably periodically interrogated one after the other which corresponds to a scanning procedure.

In the embodiment of FIG. 2 a strip-like light source 12' is imaged via a condensor 21, a beam divider 22, a strip-like deflecting mirror 32 and the transmitter-side concave mirror 14 onto the surface of the web 11 as the strip of illumination 13. The light source can be a lamp with an extended filament or a capillary lamp. With this arrangement a defined strip of illumination is thus generated on the surface of the web 11. The condensor, which here determines the inlet pupil 16, is, in this embodiment, arranged at the optical spacing of the focal length from the transmitter-side concave mirror 14, so that beams which are parallel to one another emerge from the transmitter-side concave mirror 14 in the direction of the strip of illumination.

Whereas the beam divider 22 deflects the light beam coming from the condensor 21 downwardly by about 90°, a scanning light beam 28 is incident on the beam divider 22 at an angle of approximately 90° to the light beam coming from the condensor 21. The scanning light beam 28 is generated by a mirror wheel 26 which rotates at high speed in the direction of the illustrated arrow with its reflecting mirror surface being arranged at the distance of the focal length from the transmitter-side concave mirror 14. The mirror wheel is illuminated by a laser 27 via a plane deflecting mirror 36 and a beam widening optical system 37. The scanning arrangement comprising the laser 27, the beam widening optical system 37, the plane deflecting mirror 36 and the mirror wheel 26 is dimensioned so that the sharp scanning light bead generated in the region of the strip of illumination 13 cyclically scans the material web 11 along the strip of illumination 13 in the transverse direction of the web during rotation of the mirror wheel 26.

In this way two apparatuses for generating a continuous strip of light and a strip of light generated by a scanning light bead are interleaved, with all optical elements from the beam divider 22 on being used twice.

On the receiver side, which is arranged at the angle of reflection relative to the transmitter-side concave mirror 14, there is located a strip-like receiver-side concave mirror 15 which is constructed identically to the transmitter-side concave mirror 14 and deflects the light reflected from the strip of illumination 13 at the angle of reflection, via a further plane deflecting mirror 33, into the objective 18 where the image of the entry pupil 16 is located. The diode row 17 with the electronic processing circuit 30 in accordance with the embodiment of FIG. 1 is again arranged behind the objective 18.

A further beam divider 23 is arranged in the beam path in front of the objective 18 and deflects a part of the received light to a photomultiplier 29 which is arranged at 90° to the converging received beam and is likewise connected to the electronic processing circuit 30 via a line 38.

In this way the received light passes in part onto the diode row 17 and in part into the photomultiplier 29.

In order to decouple the two interleaved beam paths the two dividing mirrors are correspondingly dichromatically executed and optical filters 24, 25 are arranged in front of the objective 18 and in front of the photomultiplier 29 respectively, but behind the beam divider 23. The dividing mirrors 24, 25 respectively filter out the spectral range of the other bundle of rays. In this way it is ensured that only light emerging from the light source 12' reaches the diode row 17, while the photomultiplier 29 only receives the light from the laser 27. By appropriate spectral layout of the dividing mirror 22, and/or of a suitable filter 24 which can be arranged at the entry pupil 16, it is possible to further favourably influence the spectral separation of the two received beams.

With the apparatus of FIG. 2 one and the same linear region along the strip of illumination 13 can be monitored by a stationary monitoring apparatus with the light source 12' and by a dynamic scanning apparatus with the laser 27'. In this way coarser faults, the extent of which is not too small, but which produce smaller light deflection or colour deviations, can be detected by means of the stationary monitoring apparatus, while the laser scanner detects the finest faults with large scattering angles.

We claim:

1. An optical web monitoring apparatus comprising: an illumination arrangement including a light source, and a transmitter-side strip-like concave mirror illuminated by said light source, for generating a strip of illumination on a surface of a moving elongated web spaced from the transmitter-side concave mirror, the strip of illumination extending transverse to the longitudinal direction of the web, a light receiving arrangment including an optical system, a photo-receiver arrangment formed by a line of diodes, and an electronic processing circuit, said light receiving arrangement projecting light emerging from the strip of illumination via said optical system onto said photoreceiver arrangement which delivers electrical signals corresponding to the received light to said electronic processing circuit, said transmitter-side concave mirror forming an image of an entry pupil of a total beam path from said light source at a location within the beam path extending from the light source to the photoreceiver arrangement, at a substantial distance behind the strip of illumination, in an objective located in front of the line of diodes, the objective imaging the strip of illumination onto the line of diodes in such a way that the strip-like image of the strip of illumination extends in the longitudinal direction of the line of diodes.

2. An apparatus in accordance with claim 1, wherein a point light source is arranged at the entry pupil for generating the strip of illumination via said transmitter-side concave mirror which is vignetted transverse to its longitudinal direction.

3. An apparatus in accordance with claim 1, wherein a point light source is imaged via a strip-like condensing concave mirror extending optically parallel to the transmitter-side concave. mirror at an aperture diaphragm arranged at the location of the entry pupil; the light emerging through the aperture diaphragm generating the strip of illumination via the transmitter-side concave mirror.

4. An apparatus in accordance with claim 1, without optical image forming elements between the concave mirror and the objective.

5. An apparatus in accordance with claim 3, wherein the strip of illumination is located approximately between ⅓ to ½ of the beam path between the transmitter-side concave mirror and the objective.

6. An optical web monitoring apparatus according to claim 1, comprising further optical image forming means in addition to said objective.

7. An apparatus in accordance with claim 6, wherein the further optical image forming includes a receiver-sde strip-like concave mirror in the light receiving arrangement.

8. An apparatus in accordance with claim 7, wherein the receiver-side strip-like concave mirror has a focal lenght equalling that of the transmitter-side concave mirror.

9. An apparatus in accordance with claim 7, the beam path between the transmitter-side concave mirror and the receiver-side concave mirror extends in parallel manner.

10. An apparatus in accordance with claim 6, comprising a line-like light source imaged via a condensor and the transmitter-side concave mirror onto the surface of the web to form the strip of illumination.

11. An apparatus in accordance with claim 1, wherein the strip of illumination extends across the whole width of the web.

12. An apparatus in accordance with claim 6, wherein the strip of illumination extends across the whole width of the web.

13. An apparatus in accordance with claim 7, comprising a beam divider between the entry pupil and the transmitter-side concave mirror; a mirror wheel or a rotary mirror arraanged at a distance from the transmitter-side concave mirror corresponding to the focal length thereof, and a laser for generating a scanning beam which reaches the transmitter-side concave mirror from where the scanning beam is projected obliquely onto the web in the region of the strip of illumination.

14. An apparatus in accordance with claim 7, comprising a beam divider between the receiver-side concave mirror and the objective for dividing the received beam into a first beam to the objective and a second beam deflected onto a photoreceiver connected to the electronic processing circuit.

15. An apparatus in accordance with claim 14, wherein said photoreceiver is a photo-multiplier.

16. An apparatus in accordance with claim 14, comprising optical filters tuned to non-overlapping spectral ranges, between the beam divider, and respectively the objective and the photoreceiver, for decoupling the first and second beams.

17. An apparatus in accordance with claim 14, comprising diachromatic dividing mirrors tuned to non-overlapping spectral ranges, between the beam divider, and respectively the objective and the photoreceiver, for decoupling the first and second beams.

18. An apparatus in accordance with claim 14, comprising optical filters and diachromatic dividing mirrors tuned to non-overlapping spectral ranges, between the beam divider, and respectively the objective and the photoreceiver, for decoupling the first and second beams.

19. An apparatus in accordance with claim 1, wherein the ratio of the image of the entry pupil in the objective amounts to 0.5:1 to 1:2.

20. An apparagus in accordance with claim 6, wherein the ratio of the image of the entry pupil in the objective amounts to 0.5:1 to 1:2.

21. An apparatus in accordance with claim 6, comprising at least one plane, strip-like deflecting mirror in the beam path.

22. An apparatus in accordance with claim 6, comprising a plurality of diaphragms matched to one another in the entry pupil and in the objective.

* * * * *